United States Patent
Lang et al.

[19]

[11] Patent Number: 6,153,178
[45] Date of Patent: *Nov. 28, 2000

[54] AGENT AND PROCESS FOR PERMANENT HAIR WAVE BASED ON MERCAPTOACETAMIDES

[75] Inventors: Guenther Lang, Reinheim; Beate Dannecker, Darmstadt; Wolfgang Hanefeld, Marburg/Lahn; Heiko Walther, Marburg/Lahn, all of Germany

[73] Assignee: Wella Aktiengesellschaft, Darmstadt, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/981,367

[22] PCT Filed: Mar. 1, 1997

[86] PCT No.: PCT/EP97/01028

§ 371 Date: Dec. 19, 1997

§ 102(e) Date: Dec. 19, 1997

[87] PCT Pub. No.: WO97/41828

PCT Pub. Date: Nov. 13, 1997

[30] Foreign Application Priority Data

May 8, 1996 [DE] Germany .............. 196 18 445

[51] Int. Cl.$^7$ .............. A61K 7/09; A61K 7/11; A61K 7/13
[52] U.S. Cl. .............. 424/70.1; 424/70.2; 424/70.4; 424/70.5
[58] Field of Search .............. 424/70.2–70.5, 424/70.1

[56] References Cited

U.S. PATENT DOCUMENTS 4,642,306  2/1987  Rosa et al. .............. 514/222

FOREIGN PATENT DOCUMENTS 948 186  8/1956  Germany .
972 424  7/1959  Germany .

*Primary Examiner*—Thurman K. Page
*Assistant Examiner*—Lakshmi Channavajjala
*Attorney, Agent, or Firm*—Michael J. Striker

[57] ABSTRACT

The aqueous composition for permanent hair-styling has a pH of from 6.5 to 9.5 and contains from 3 to 28% by weight of a compound of formula I,

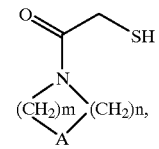

(I)

wherein A represents —$CH_2$—, —C=O—, —S—, —O— and —NR— and R is an alkyl group having from 1 to 6 carbon atoms or a hydroxyalkyl group having from 1 to 6 carbon atoms, m is an integer from 1 to 3 and n is an integer from 0 to 3, with the proviso that n=0 only when A is methylene; water and one or more cosmetic additive ingredient selected from the group consisting of thickening agents, anionic surfactants, cationic surfactants, amphoteric surfactants, nonionic surfactants, opacifiers, alcohols, sugars, solubilizers, stabilizers, buffer substances, perfume oils, colorants, hair conditioning and hair treatment ingredients.

6 Claims, No Drawings

AGENT AND PROCESS FOR PERMANENT HAIR WAVE BASED ON MERCAPTOACETAMIDES

BACKGROUND OF THE INVENTION

1. Field of the Invention

This application is a 371 of PCT/EP97/01028, filed Mar. 1, 1997.

The present invention subject matter of the invention concerns a composition for permanent hair-styling, characterized in that as a keratin-reducing agent it contains a compound of the general formula

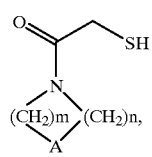

(I)

in which A stands for —$CH_2$—, C=O, —S—, —O—, —NR—, where R=$C_1$ to $C_6$ alkyl or $C_1$ to $C_6$ hydroxyalkyl, n stands for an integer from 0 to 3, on the condition that n stands for zero only if A=—$CH_2$—, and m stands for an integer from 1 to 3, and to a method for permanent hair-styling using such means.

2. Prior Art

The classical technique for achieving permanent hair-styling is known to be based on two treatment steps: In the first step, the cystine disulfide bridges of the keratin in the hair are opened by the action of a composition that includes a reducing agent (styling means). The hair is then put in the desired style. In a second step, cystine disulfide bonds are closed again, using a fixative, that is, an agent that contains an oxidizing active ingredient.

As the pioneering work in German Patents 948186 and 972424 show, thioglycolic acid, for instance in the form of an ammonium or monoethanolamine salt, is used as a classical permanent-wave reducing agents. Other typical reducing active ingredients are inorganic sulfites, 2-mercaptopropionic acid (thiolactic acid), 3-mercaptopropionic acid, certain mercaptocarboxylic acid esters, cysteine, and derivatives of these compounds.

However, all of these composition and agents have a number of disadvantages. Alkaline preparations on the basis of mercapto acetamides, despite adequate action, cause hair damage, which is expressed for instance in increasing hair breakage. Often, these composition and agents also undesirably stress the scalp.

Finally, the unpleasant smell of the reducing agents used requires intensive perfuming of the products. Using 2-mercaptopropionic acid (thiolactic acid) allows one to solve some of these problems. However, thiolactic acid in comparison with the generally used thioglycolic acid is distinguished by weaker shaping action.

The mercaptocarboxylic acid esters that allow hair-styling even at relatively low pH values are not satisfactory in terms of their coloration by the skin and their risk of sensitization. Instead of mercaptocarboxylic acid esters, mercaptocarboxylic acid amides have also been used, such as thioglycolic acid amide or alkyl- or hydroxyalkyl-substituted mercaptocarboxylic acid amides. These substances, like the mercaptocarboxylic acid esters, have a high shaping potential even at relatively low pH values, but with regard to sensitization are even more critical than the mercaptocarboxylic acid esters.

SUMMARY OF THE INVENTION

It has now surprisingly been discovered that these disadvantages can be avoided by using the aforementioned mercapto acetamides on the basis of cyclical amines, and that they have an even greater shaping potential than thiolactic acid.

The subject of the present invention is therefore a means for permanent hair-styling, characterized in that as a keratin-reducing agent it contains a compound of the general formula

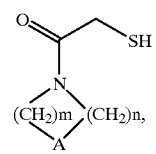

(I)

in which A stands for —$CH_2$—, C=O, —S—, —O—, —NR—, where R=$C_1$ to $C_6$ alkyl or $C_1$ to $C_6$ hydroxyalkyl, n stands for an integer from 0 to 3, on the condition that n stands for zero only if A=—$CH_2$—, and m stands for an integer from 1 to 3.

Compounds of the above formula (I) that are preferentially used are those of the following general formulas

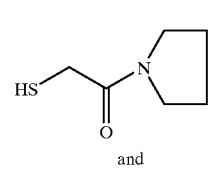

(II)

and

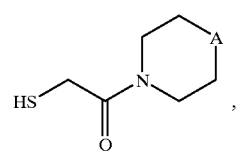

(III)

where A stands for —$CH_2$—, —O—, —S—, or —NR—, where R=$C_1$ to $C_6$ alkyl or $C_1$ to $C_6$ hydroxyalkyl.

Production methods for the mercapto acetamides of formula (I) are to some extent described in the literature. In the method of the invention, the production is achieved by reacting the corresponding amines with methyl thioglycolate in a protective gas atmosphere, extraction in a suitable solvent, and ensuing short-course distillation.

The mercapto acetamides contained in the composition of the invention are preferably used in the composition for permanent hair-styling that is ready for use in a quantity from 3 to 28 weight %, and especially preferably in a quantity of from 5 to 21 weight %.

In a further embodiment of the invention, the mercapto acetamides may also be used in a mixture with other known thiols, such as thioglycolic acid, thiolactic acid, cysteine, cysteamine, alkyl- or acylcysteamines, or sulfites.

The hair-styling composition ready for use preferably have a pH of from 6.5 to 9.5 and especially preferably from 6.5 to 8.5. As alkalizing agents or as composition for adjusting the pH value, ammonia or sodium hydroxide solution are especially suitable, but all other water-soluble, physiologically tolerable salts of organic and inorganic bases, such as ammonium hydrogen carbonate, can also be considered.

The styling composition may be packaged as a single, dual, or three-component preparation, and the composition may be either in the form of an aqueous solution or of an emulsion, or in thickened form on an aqueous base, in particular in the form of a cream, gel or paste.

The composition according to the invention can thus be obtained for instance by mixing two components, of which the first component contains at least one alkalizing agent, such as an alkali carbonate, ammonium carbonate, alkali hydrogen carbonate, or ammonium hydrogen carbonate, and a mercapto acetamide of formula (I), and the second component contains at least one of the cosmetic additives listed below, plug water.

It is also possible to package the composition according to the invention is the form of a three-component preparation, where one component contains some of the cosmetic additives listed below as well as water, a second, water-free component contains a mercapto acetamide of formula (I), and the third component contains further additives, such as perfume oils, solubilizers and treatment preparations, in a aqueous solution or in a water-free form.

In all the embodiments of the composition of the invention, the cosmetic additives may be contained in either the aqueous or the nonaqueous component or components.

Naturally, the styling composition may contain all the usual known additives for such composition, such as thickening agents such as bentonite, fatty acids, starch, polyacrylic acid and its derivatives, cellulose derivatives, alginates, vaseline, and paraffin oils; wetting agents are emulsifiers selected from the classes of anionic, cationic, amphoteric or nonionic surfactants, such as fatty alcohol sulfates, fatty alcohol ether sulfates, alkyl sulfonates, alkyl benzene sulfates, quaternary ammonium salts, alkyl betaines, ethoxylated alkyl phenols, fatty acid alkenolamides or ethoxylated fatty acid esters; also opacifiers, such as polyethylene glycol ester;

alcohols, such as ethanol, propanol, isopropanol and glycerine; sugar, such as D-glucose; solubilizers, stabilizers, buffer substances, perfume oils, colorants, and hair conditioning and treatment ingredients, such as cationic polymers, lanolin derivatives, cholesterol, pantothenic acid, and betaine.

The aforementioned ingredients are used in the typical quantities for such purposes; for instance, the wetting agents and emulsifiers may be contained in concentrations of a total of 0.2 to 30 weight %; the alcohols may be contained in a quantity of a total of 0.1 to 20 weight %; the opacifiers, perfume oils and colorants may be contained in a quantity of 0.01 to 1 weight % each; the buffer substances may be contained in a quantity of a total of 0.1 to 10 weight %; and sugar, solubilizers, stabilizers and hair conditioning and treatment ingredients may be contained in a quantity of from 0.1 to 5 weight % each, while the thickening agent and solubilizers may be contained in a quantity of a total of 0.5 to 20 weight % in this composition.

Moreover, to increase the effect, so-called swelling and penetration substances may be added to this composition, examples being dipropylene glycol monomethyl ether, 2-pyrrolidone or imidazolidin-2-one, in a quantity from 1 to 30 weight %, and to prevent frizziness dithio compounds are added, such as dithiodiglycolic acid, dithiolactic acid, the dithiols of the aforementioned compounds or the respective salts.

By varying the pH value, a composition can be made available that is universally suited for any hair structure, optionally with the additional action of heat. The composition brings about an elastic, permanent, uniform reshaping from root of the hair to its tips, without causing allergic or sensitizing reactions.

The present invention also relates to a method for permanent hair-styling, in which the hair, before and/or after it is set in the desired style, is treated with a styling composition, rinsed with water, oxidatively post-treated, again rinsed with water, optionally set for water-waving and then dried, which is characterized in that as the styling composition, the above-described composition of the invention are used.

In a preferred embodiment of the method of the invention, the hair is first washed with a shampoo and the rinsed with water. Then, the towel-dried hair is split into individual strands and wound onto rollers with a diameter of from 5 to 30 mm, preferably 5 to 15 mm. The hair is then treated with a quantity of the described styling means according to the invention in a quantity suitable for the hair styling, preferably 60 to 120 g.

After an action time that is adequate for permanent hair-styling, which can take from 5 to 30 minutes (to to 30 minutes without the action of heat; 5 to 20 minutes with the action of heat), depending on the nature of the hair, the pH value and the styling effectiveness of the styling means as well as on the application temperature, the hair is rinsed with water and then oxidatively post-treated ("fixed"). Depending on the fullness of the hair, the post-treating means is preferably used in a quantity of from 80 to 100 g.

For the oxidative post-treatment in the state in which the hair is set on rollers or has been unwound from the rollers, any arbitrary post-treatment means suitable for such treatment may be used. Examples of oxidants usable for used post-treatment means are potassium bromate and sodium bromate, sodium perborate, urea peroxide, and hydrogen peroxide. The concentration of the oxidant varies as a function of the application time (as a rule 5 to 15 minutes) and the application temperature. Normally, in the aqueous post-treatment means ready for use, the oxidant is present in a concentration of from 0.5 to 10 weight %. The means for the oxidative post-treatment may naturally include other substances, such as wetting agents, treatment preparations such as cationic polymers, weak acids, buffer substances or peroxide stabilizers, and may be in the form of an aqueous solution, an emulsion, or in thickened form on an aqueous base, in particular in the form of cream, gel or paste. These typical additives may in particular be contained in the post-treatment means in a quantity of from 0.1 to 10 weight %.

Next, the rollers are removed. If necessary, the hair unwound from the rollers can be oxidatively post-treated once again. The hair is then rinsed with water, optionally set on rollers with water, and finally dried.

The following examples are intended to explain the subject of the invention in further detail but without limiting the subject to these examples.

EXAMPLES

Example 1

Production of the Mercapto Acetamides

Two mols of the applicable primary or secondary amine are placed in a 500 ml triple-neck flask. During cooling in a water bath, one mol of methyl thioglycolate is added slowly, drop by drop, so that the temperature does not exceed 30° C. The starting batch is flushed with argon and stirred until the methyl thioglycolate has reacted in quantity (monitored by thin-film chromatography on Merck DC aluminum foils 5×10 cm in size; silica gel 60 F 254).

The mixture is acidified (pH 24) with 36% hydrochloric acid while cooling with ice, and exhaustively extracted with ethyl acetate. The solvent is distilled off in a vacuum in the recirculating evaporator, the residue is brought to pH 7.0 by adding sodium hydroxide solution, and is shaken out again with ethyl acetate. The united fractions are then dried over sodium sulfate and inspissated. The residue is distilled to make the pure product using a short-course distillation apparatus at a maximum of 0.01 Torr. This procedure has decisive significance if the purest possible product is to be obtained with a good yield. Contamination from incompletely reacted educts, as well as cleavage products from thermolysis or hydrolysis should be avoided, because of their sensitizing properties, and this can be done only by careful distillation.

| Amine component | Yield in % | Elemental analysis, calculated/found | | | | HPLC (FP) | Boiling point |
| --- | --- | --- | --- | --- | --- | --- | --- |
| 1. Pyrrolidine | 76 | C: 49.63 | H: 7.63 | N: 9.65 | S: 22.08 | 96.818 | 103° C. at 0.05 Torr |
| | | C: 49.40 | H: 7.52 | N: 9.59 | S: 22.20 | | |
| 2. Piperidine | 42 | C: 52.80 | H: 8.23 | N: 8.80 | S: 20.13 | 94.069 | 93° C. at 0.08 Torr |
| | | C: 52.48 | H: 7.98 | N: 8.81 | S: 20.43 | | |
| 3. Morpholine | 54 | C: 44.70 | H: 6.88 | N: 8.69 | S: 19.89 | 97.313 | 98° C. at 0.07 Torr |
| | | C: 44.24 | H: 6.85 | N: 8.52 | S: 19.99 | | |

Example 2
Comparison of Waving Effectiveness

The waving effectiveness of N,N-tetramethylene mercapto acetamide was determined using glycerine monothioglycolate as a comparison substance, using waving solutions with a pH of 7, 8 and 9. To that end, prebleached and hence damaged counted strands of hair (comprising approximately 100 hairs each) and 16.5 cm long made from central European hair were wound wet onto standardized spiral rollers (inside diameter: 3 mm), and after conditioning in a climate chamber (temperature 20° C.; humidity 65%) treated with a solution of reducing agent containing 87 mmol per 100 g and adjusted to the applicable pH value. The quantity of waving fluid applied was calculated using the ratio 1:1.2 (1 g of hair 1.2 ml of waving fluid). 20 minutes was selected as the action time; the action temperature was 50° C. Next, the hair was fixed with a fixative containing peroxide, dried, and after being unwound from the rollers hung for four hours in water (water bath temperature: 40° C.).

The wave stability (WSN) is calculated by the following formula:

$$\text{Wave stability in \%} = \frac{l_o - l_t}{l_o - l_1} \times 100$$

$l_o$=total length of the unreshaped, stretched strands (16.5 cm)

$l_t$=length of the strands, unwound from the rollers and hung out, after 240 minutes $l_1$=length of the reshaped strands wound onto rollers; where the inside diameter of the roller is 3 mm, $l_1$=35 mm As a standard, small strands of hair were treated with a glycerine monothioglycolate solution adjusted accordingly to pH 9. The standardized wave stabilities given in Table I refer to this standard solution (pH=9) whose wave stability was set to 100%.

TABLE I

| | Standardized wave stabilities WSN in % | | | |
| --- | --- | --- | --- | --- |
| pH of the waving solution | WSN of thiolactic acid | WSN of N,N-3-oxapentamethylene mercapto acetamide | WSN of N,N-pentamethylene mercapto acetamide | WSN of N,N-tetramethylene mercapto acetamide |
| 7 | 57% | 82% | 87% | 78% |
| 8 | 50% | 98% | 102% | 94% |
| 9 | 70% | 95% | 104% | 100% |

Table I shows that the waving effectiveness of the mercapto acetamides of the invention is higher, at pH 7, 8 and 9, than for thiolactic acid.

Example 3
Permanent Styling Means for Colored Hair 12.0 g N,N-tetramethylene mercapto acetamide 0.4 g ammonia (25% aqueous solution) for pH adjustment 2.0 g ammonium hydrogen carbonate 2.0 g isopropanol 1.9 g isooctylphenol, ethoxylated with 10 mols of ethylene oxide 1.9 g poly(dimethyldiallyl ammonium chloride)

0.3 g perfume oil 0.1 g vinyl pyrrolidone and styrene mixed polymer (Antara 430 made by GAF Corp., New York, USA)

81.2 g water 100.0 g

The pH of this means is in the range from 7.0 to 7.5.

Hair previously damaged by color treatments is washed with a shampoo, towel-dried, and wound onto rollers with a diameter of 8 mm. Next, the above-described hair-styling means is applied uniformly to the hair wound onto the rollers. The hair is then covered with a plastic hood and heated for 10 minutes under a dryer hood at a temperature of 45° C. The covering is then removed and the hair is rinsed with water and oxidatively post-treated with 100 g of a 3% aqueous hydrogen peroxide solution. After the rollers are removed, the hair is rinsed again with water, set on rollers with water, and then dried.

The outcome of this treatment is a uniform, elastic and durable reshaping of the hair.

Example 4
Permanent Styling Means for Normal Hair 17.5 N,N-pentamethylene mercapto acetamide 8.9 g ammonia (25% aqueous solution)

5.0 g ammonium hydrogen carbonate 4.0 g urea 2.4 g monoethanolamine 1.5 g isooctylphenol, ethoxylated with 10 mols of ethylene oxide 0.5 g poly(dimethyldiallyl ammonium chloride)

0.5 g perfume oil 0.1 g vinyl pyrrolidone and styrene mixed polymer (Antara 430 made by GAF Corp., New York, USA)

59.6 g water 100.0 g

The pH of this means is 8.4.

Normal, undamaged hair is washed, dried with a hand towel, and set on rollers with a diameter of 6 mm. The hair is then uniformly moistened thoroughly with the hair-styling means described above. After an action time of 15 minutes, the hair is rinsed thoroughly with water and then oxidatively post-treated with 80 g of a 3% aqueous hydrogen peroxide solution. After the rollers are removed, the hair is rinsed again with water, set on rollers with water, and then dried.

The hair thus treated has a uniform, bouncy curl.

Example 5
Permanent Styling Means for Normal Hair 17.5 g N,N-tetramethylene mercapto acetamide 8.9 g ammonia (25% aqueous solution)

5.0 g ammonium hydrogen carbonate 2.0 g D-glucose 2.4 g ammonia 1.5 g isooctylphenol, ethoxylated with 10 mols of ethylene oxide 0.5 g poly(dimethyldiallyl ammonium chloride)

0.5 g perfume oil 0.1 g vinyl pyrrolidone and styrene mixed polymer (Antara 430 made by GAF Corp., New York, USA)

61.6 g water 100.0 g

The pH of this means is 8.0 to 8.5.

Normal, undamaged hair is washed, dried with a hand towel, and set on rollers with a diameter of 6 mm. The hair is then uniformly moistened thoroughly with the above-described hair-styling means. After an action time of 15 to 25 minutes, the hair is rinsed thoroughly with water and then oxidatively post-treated with 80 g of a 3% aqueous hydrogen peroxide solution. After the rollers are removed, the hair is rinsed again with water, set on rollers with water, and then dried.

The hair thus treated has a uniform, bouncy curl.

What is claimed is:

1. An aqueous composition for permanent hair-styling, said composition having a pH of from 6.5 to 9.5 and comprising from 3 to 28% by weight of a compound of formula II

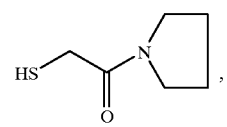

or a compound of Formula III

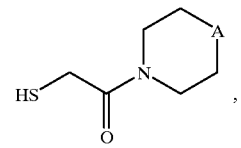

wherein A represents —CH$_2$—, —S— or —O—;

water; and at least one cosmetic additive ingredient selected from the group consisting of thickening agents, anionic surfactants, cationic surfactants, amphoteric surfactants, nonionic surfactants, opacifiers, alcohols, sugars, solubilizers, stabilizers, buffer substances, perfume oils, colorants, hair conditioning and hair treatment ingredients.

2. The aqueous composition means as defined in claim 1 containing at least one keratin reducing agent and said at least one keratin reducing agent consists only of said compound of formula II or said compound of formula III.

3. A method of permanent hair-styling of hair, said method comprising the steps of:

a) providing an aqueous hair treatment composition having a pH of from 6.5 to 9.5 and comprising from 3 to 28% by weight of a compound of formula II

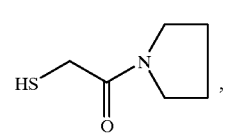

or a compound of formula III

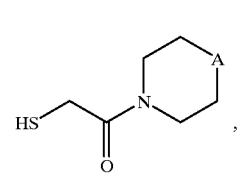

wherein A represents —CH$_2$—, —S— or —O—;

water and at least one cosmetic additive ingredient selected from the group consisting of thickening agents, anionic surfactants, cationic surfactants, amphoteric surfactants, nonionic surfactants, opacifiers, alcohols, sugars, solubilizers, stabilizers, buffer substances, perfume oils, colorants, hair conditioning and hair treatment ingredients;

b) setting the hair in a desired hair style;

c) before or after the setting of the hair in step b), applying said hair treatment means to the hair in an amount suitable for a permanent hair styling of the hair;

d) after the applying of step c), allowing the hair treatment composition to act on the hair for from 5 to 30 minutes without heat or from 5 to 20 minutes with heat;

e) after the allowing of step d), rinsing the hair with water;

f) performing an oxidative after-treatment of the hair; and g) rinsing the hair again with water.

4. The method as defined in claim 3, further comprising after the oxidative after-treatment setting the hair in a water wave and drying.

5. The method as defined in claim 3, wherein said amount of said hair treatment means applied to said hair is from 60 to 120 g.

6. The method as defined in claim 3, wherein said oxidative after-treatment comprises applying an aqueous oxidizing means to said hair and allowing said oxidizing means to act on the hair for from 5 to 15 minutes, wherein said aqueous oxidizing means includes an oxidizing agent selected from the group consisting of potassium bromate, sodium bromate, sodium perborate, urea peroxide and hydrogen peroxide.

* * * * *